(12) United States Patent
Sozzi

(10) Patent No.: US 7,888,008 B2
(45) Date of Patent: Feb. 15, 2011

(54) METHOD FOR THE DETECTION OF CANCER

(75) Inventor: Gabriella Sozzi, Milan (IT)

(73) Assignee: Istituto Nazionale per Lo Studio E La Cura Dei Tumori, Milan (IT)

( * ) Notice: Subject to any disclaimer, the term of this patent is extended or adjusted under 35 U.S.C. 154(b) by 1285 days.

(21) Appl. No.: 10/538,495

(22) PCT Filed: Dec. 22, 2003

(86) PCT No.: PCT/EP03/14719
§ 371 (c)(1),
(2), (4) Date: Apr. 13, 2006

(87) PCT Pub. No.: WO2004/057024
PCT Pub. Date: Jul. 8, 2004

(65) Prior Publication Data
US 2007/0148644 A1    Jun. 28, 2007

(30) Foreign Application Priority Data
Dec. 23, 2002    (IT) .................... MI2002A2743

(51) Int. Cl.
*C12Q 1/68*    (2006.01)
*C12P 19/34*    (2006.01)
*C07H 21/04*    (2006.01)

(52) U.S. Cl. .................... 435/6; 435/91.2; 536/22.1; 536/24.3

(58) Field of Classification Search ................ 536/22.1, 536/24.3; 435/6, 91.2
See application file for complete search history.

(56) References Cited

U.S. PATENT DOCUMENTS

| | | | | |
|---|---|---|---|---|
| 6,156,504 | A * | 12/2000 | Gocke et al. .................... | 435/6 |
| 6,475,789 | B1 * | 11/2002 | Cech et al. .................. | 435/366 |
| 6,664,046 | B1 * | 12/2003 | Chang et al. .................... | 435/6 |
| 7,160,996 | B1 * | 1/2007 | Cook ........................ | 536/24.3 |
| 7,163,789 | B2 * | 1/2007 | Chen et al. ..................... | 435/6 |

FOREIGN PATENT DOCUMENTS

| | | |
|---|---|---|
| EP | 1 158 055 A1 | 11/2001 |
| WO | WO-99/41406 A1 | 8/1999 |

OTHER PUBLICATIONS

Wick et al. Gene, 1999, vol. 232, p. 97-106.*
Buck et al. BioTechniques, 1999, vol. 27(3), p. 528-536.*
Nucleic acid sequence search reports.*
Lowe et al. Nucleic acid research, 1990, vol. 18(7), p. 1757-1761.*
The nucleic acid sequence search repport for SEQ ID No. 1 and 3.*
Dasi et al. Laboratory Investigation, 2001, vol. 81(5), p. 767-769.*
Anker et al. Clinica Chimica Acta, 2001, vol. 313, p. 143-146.*
Sozzi G et al., Cancer Research, vol. 61, Jun. 15, 2001, pp. 4675-4678.
Kok De J B et al., Clinical Chemistry, American Association for Clinical Chemistry, vol. 46, No. 3, Mar. 2000, pp. 313-318.
Thijssen M A M A et al., Anticancer Research, Helenic Anticancer Institute, vol. 22, No. 1A, Jan. 2002, pp. 421-425.
Lo Y M D et al., Clinical Chemistry, American Association for Clinical Chemistry, vol. 46, No. 3. Mar. 2000, pp. 319-323.
Kopreski M et al., Clinical Cancer Research, The American Association for Cancer Research, vol. 5, Aug. 1999, pp. 1961-1965.
Anker P et al., Cancer and Metastasis Reviews, Kluwer Academic Publishers, vol. 18, No. 1 1999, pp. 65-73.
Sozzi et al., "Quantification of Free Circulating DNA As a Diagnostic Marker in Lung Cancer," Journal of Clinical Oncology, vol. 21, No. 21, pp. 3902-3908 (2003).
Diehl et al., "Detection and Quantification of Mutations in the Plasma of Patients with Colorectal Tumors," Proc. Natl. Acad. Sci. USA, vol. 102, No. 45, pp. 16368-16373 (2005).
Andriani et al., "Detecting Lung Cancer in Plasma with the use of Multiple Genetic Markers," Int. J. Cancer, vol. 108, pp. 91-96, (2004).
Bunn Jr., "Editorial: Early Detection of Lung Cancer Using Serum RNA or DNA Markers: Ready for "Prime Time" or for Validation?" Journal of Clinical Oncology, vol. 21, No. 21, pp. 3891-3893, (2003).

* cited by examiner

*Primary Examiner*—Kenneth R. Horlick
*Assistant Examiner*—Joyce Tung
(74) *Attorney, Agent, or Firm*—Birch, Stewart, Kolasch & Birch, LLP.

(57) ABSTRACT

A method for the early diagnosis, prognosis or clinical monitoring of cancer disease based on the quantitation of DNA in a plasma sample from a cancer patient, a subject with cancer susceptibility or an individual at risk of developing cancer.

10 Claims, 3 Drawing Sheets

Percentile distribution of plasma DNA concentration in ng/ml from the disease status

|  | mini | 10° | 25° | mediana | 75° | 90° | max | media | sd |
|---|---|---|---|---|---|---|---|---|---|
| case | 0.5 | 9 | 15.8 | 24.3 | 43.7 | 65.9 | 3010 | 75* | 310* |
| control | 0.1 | 0.4 | 1.1 | 3.1 | 6.3 | 11.1 | 27 | 4.6 | 5 |
| | | | | | | | | 37.4 | 45.7 |

* values excluded 2 outliers (823 and 3010 ng/ml).

METHOD FOR THE DETECTION OF CANCER

The present invention provides a method in vitro for the early diagnosis, prognosis and monitoring of cancer, or for the determination of the risk of development of cancer. The method of the invention is based on the quantification of DNA in a plasma sample through PCR amplification.

BACKGROUND ART

A number of scientific or patent publications describe methods for detecting cancer based on the identification of specific genetic alterations of circulating DNA or RNA.

U.S. Pat. No. 5,496,699 discloses a method for detecting mutations in nucleic acid sequences, in particular the sequence of the K-ras gene, in biological fluids such as blood, serum or plasma.

U.S. Pat. No. 5,068,175 discloses a method for detecting the presence of ras oncogene related malignancies in which said gene is quantified in serum or plasma samples.

WO01/42504 discloses the determination of extracellular nucleic acid, for example DNA of K-ras and APC genes, in serum or plasma samples, for the evaluation of the risk factor related with a number of neoplastic diseases.

WO02/18652 discloses a method of quali/quantitative detection of human telomerase RNA and telomerase reverse transcriptase RNA in plasma or serum for the diagnosis, monitoring, treatment or evaluation of a number of neoplastic diseases.

In principle, the methods for the molecular characterization of gene alterations have low sensitivity and require the analysis of a large panel of gene markers to obtain an acceptable information level.

Recently, a method has been reported for the quantitation of circulating naked DNA in plasma from lung cancer patients, based on a colorimetric assay able to discriminate between patients and healthy subjects and to early detect the relapse of the disease during follow-up (Sozzi, G. et al., Cancer Research 61, 4675-4678, Jun. 15, 2001). The colorimetric techniques (e.g. DNA Dipstick) for the quantitative evaluation of circulating DNA, however, are limited by a narrow linearity in the range 0.1-10 ng/ml, and by reduced sensitivity to lower values. In addition the test reading relies on subjective evaluation.

A more recent paper (Hsueh-Wei Chang et al., Journal of the National Cancer Institute, Vol. 94, No. 22, Nov. 20, 2002) suggested the analysis of DNA concentration in plasma samples and the analysis of SNPs for the detection of neoplastic disease, in particular ovarian cancer. DNA quantitation has been carried out by analysis of fluorescence intensity generated by the dye PicoGreen® linked to double-stranded DNA. The results show that, contrary to SNP analysis, the method used for measuring plasma DNA concentration is poorly sensitive and specific, and therefore is not suitable for the screening of population for neoplastic disease.

SUMMARY OF THE INVENTION

The present invention provides a method for the quantitative determination of circulating DNA in a plasma sample from a cancer patient, a subject with familiar cancer susceptibility or at risk of developing cancer, which comprises:
1) extracting the DNA from the sample;
2) adding to the DNA preparation: a) a mixture of oligonucleotide primers suitable for PCR amplification of a fragment of the human telomerase reverse transcriptase (hTERT) gene, and b) an oligonucleotide probe, having at least one quencher and one reporter fluorophore at the 3' and 5' ends, annealing to a sequence within the region delimited by the primers, in suitable conditions for carrying out a PCR reaction,
3) adding a heat-stable DNA polymerase with 5'-3' hexonuclease activity and amplificating the hTERT gene fragment;
4) measuring the produced fluorescence.

The relative amount of DNA present in the tested sample can easily be obtained by the detected fluorescence values by interpolation of a calibration curve obtained with known amounts of DNA.

According to a preferred embodiment, primers and probes are designed so as to amplify the fragment 13059-13156 of the hTERT gene (GenBank accession n. AF128893).

The described procedure, known as real-time PCR, can be automatically carried out using the apparatus GeneAmp 5700 Detection System (Applied Biosystem), which provides accurate quantitative DNA amplification through continuous optical monitoring of the fluorogenic PCR reaction, and it can quantify up to 1 genome-equivalent, corresponding to 6 pg of genomic DNA.

The quantitation method of circulating DNA according to the invention can be applied to the early diagnosis, prognosis or clinical monitoring of patients with different kinds of cancer, including colon-rectum, head-neck, liver and pancreas cancer, particularly lung cancer. The method of the invention can also be used for the determination of the risk or likelihood of developing cancer in healthy subjects exposed to environmental or life-style risk-factors such as, in case of lung cancer, cigarette smoking. An increase in plasma DNA of these subjects is predictive of increased risk and therefore should prompt to repeat the test on an independent plasma sample, or to more thorough and specific clinical investigations.

DETAILED DESCRIPTION OF THE INVENTION

A simple, accurate method in vitro has been found for the determination of the presence of a neoplastic disease or for the evaluation of the risk connected with development of cancer, by quantitation of plasma DNA using the real-time PCR technique. More precisely, the invention provides a method for the quantitation of circulating DNA by continuous optical monitoring of a fluorogenic PCR reaction carried out on a plasma sample, using as primers and probes oligonucleotides which couple with the human telomerase reverse transcriptase (hTERT) gene. The amplification rate of hTERT is used as an indication of the DNA total amount in the tested sample.

The procedure has been validated in a large case-control study (200 subjects) involving patients with early stage lung cancer, in which during follow-up plasma DNA levels were determined after cancer resection, and healthy, heavy smokers matched by age, sex and smoking habits. The results of the study show that 1) the method of the invention has high specificity and sensitivity, as evidenced by the AUC and ROC curves (global value: 0.94, interval 0.907-0.973), 2) in patients, including those with very early stage cancer (stage IA), the values of circulating plasma DNA are approx. 8 fold higher than those found in healthy subjects, 3) in patients monitored during cancer resection follow-up, the DNA levels rapidly decrease down to a value similar to that observed in healthy subjects; in contrast, an increase up to 20 fold has been found in individuals with recurrent cancer or metastasis.

Although the highest sum of sensitivity (90%), specificity (86%), positive predictive value (PPV-90%) and negative predictive value (NPV-90%) was obtained with a DNA concentration value of 9 ng/ml, the confidence intervals (CIs) around these diagnostic indicators overlap with those of adjacent concentrations. The selection of the optimal cutpoint will therefore have to acknowledge this variability. The value of 25 ng/ml is the only cut-point shown with sensitivity that does not overlap with that of other cut-points, although it shows a low sensitivity (46%, 95% CI, 36%, 56%).

The magnitude of reported ORs (Odd Ratios) proves the strong association between plasma DNA concentration and NSCLC risk, despite wide confidence limits. Similar OR values were never previously reported for any biological marker and could be of substantial benefit in clinical practice. Increased amounts of circulating plasma DNA were observed in samples from any stage and tumor size. This is particularly relevant for small lesions, whose systematic detection could help reducing lung cancer morbidity and mortality.

One important aspect of the quantitative analysis provided by the invention is the possibility to follow longitudinal changes after cancer resection. The data available on 35 cancer patients showed a rapid decrease of circulating DNA values after lung resection. On the contrary, no decreasing or increasing levels of plasma DNA identified subjects with recurrence of their disease (24.7 ng/ml vs. 7.1 ng/ml in cancer-free patients, p=0.002), suggesting that quantification of plasma DNA might represent a novel approach to monitor surgical patients or assess treatment efficacy after chemoradiotherapy.

To explore the possible modulation of free DNA release by smoking exposure, 20 never smokers over 55 yrs of age were analysed: their median DNA value was 0.61 ng/ml. The same analysis, carried out on the high-risk group from the case-control study (heavy smokers of age above 50, with exposure to smoke >20 pack/year) showed an average value of 4.6 ng/ml. These results indicate very low amounts of free circulating DNA in unexposed people.

The results of the clinical studies show the effectiveness of the method for the quantitation of circulating DNA of the invention in the early diagnosis of lung cancer in high-risk subjects, in particular in heavy smokers.

Calculation of the amounts of plasma DNA is based on the cycle number, where fluorescence of each reaction passes the threshold (CT), which is set to the geometric phase of the amplification above the background. The X axis denotes the cycle number of a quantitative PCR reaction. The Y axis denotes the log of fluorescence intensity over the background ($\Delta Rn$).

Figure 2:
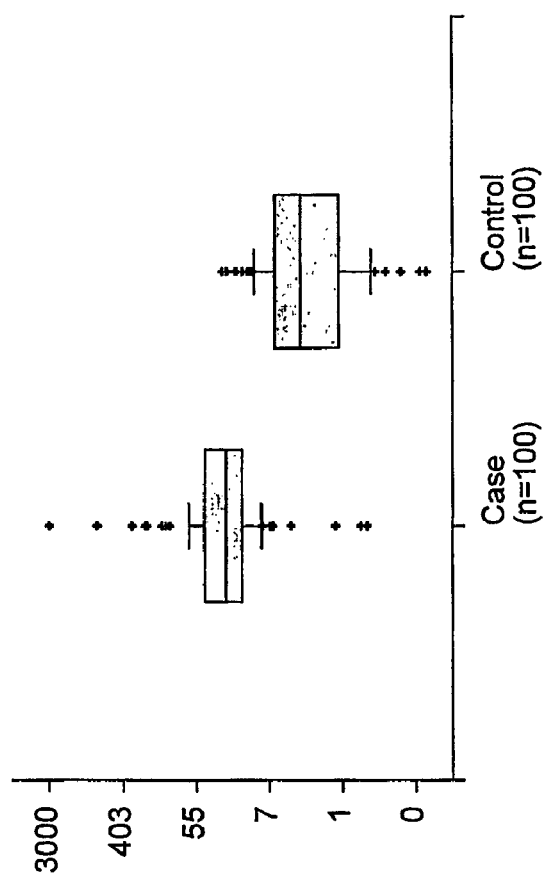

FIG. 2. Box-plots of plasma DNA concentration in NSCLC cases and matched controls. The box is bounded below and above by the 25% and 75% percentiles, the median is the solid line in the box, the lower and upper error bars indicate 90% of values. Mini=minimum value detected, max=maximum value detected, sd=standard deviation FIG. 3. ROC curves for the diagnosis of NSCLC using plasma DNA values. Curve and area under the curve (AUC) estimated using the logistic procedure in SAS (Cary, N.C.).

MATERIALS AND METHODS

Case and Control Series

One-hundred consecutive cases of non small cell lung cancer (NSCLC), 81 men and 19 women, non previously treated with chemo-radiotherapy and included in the European Institute of Oncology (IEO) tissue bank from 2000 to 2001, were evaluated. One control was selected for each case, matched by sex, age and smoking habits.

Mean age+−sd was 65.1+−8.9 years in cases and 64.1+−8.2 in controls, average smoking duration was 40.5+−10.9 years in cases and 41.7+−9.5 in controls. The population included 7 case-control pairs of never smokers. The 93 heavy smoker controls were selected among the participants to the IEO early detection program, whose chest spiral CT proved to be negative. Non smoking controls were recruited from healthy blood donors at the immuno-hematology unit of the Institute. The number of former smokers differed slightly between cases and controls (28 cases and 11 controls).

One light and occasional smoker case (<5 cigarettes per day) was matched to a never smoker. A mean within-pair difference of 1 year in age was statistically significant (p<0.02), suggesting the need to adjust for age in the analysis of plasma DNA as risk factor.

Samples Collection and DNA Isolation

A 7.5 ml sample of peripheral blood was EDTA collected from patients prior to surgery and from controls at the time of spiral CT examination, and stored at −140°. Plasma separation and DNA extraction were performed as previously reported (25). The DNA purified from 1 ml of plasma was eluted in a final volume of 50 µl of water. Testing of plasma DNA was performed without knowledge of the case/control status.

DNA Quantification in Plasma

To quantify the circulating DNA in plasma we used a real-time quantitative PCR approach based on the 5' nucleotide method. This methodology is based on continuous monitoring of a progressive fluorogenic PCR by an optical system (28'29). The PCR system uses two amplification primers and an additional, amplicon-specific, and fluorogenic hybridization probe whose target sequence is located within the amplicon.

The probe is labeled with two fluorescent dyes. One serves as a reporter on the 5'-end (VIC™ dye). Its emission spectrum is quenched by a second fluorescent dye at the 3'-end (TAMRA). If amplification occurs, the 5' to 3' exonuclease activity of the AmpliTaq© DNA polymerase cleaves the reporter from the probe during the extension phase, thus releasing it from the quencher (30). The resulting increase in fluorescent emission of the reporter dye is monitored during the PCR process.

Primers and probes were designed to specifically amplify the ubiquitous Gene of interest, the human Telomerase Reverse Transcriptase (hTERT) single copy gene mapped on 5p15.33. The amplicon size of the hTERT gene was 98 bp (position 13059-13156, of the GenBank as accession no AF128893). The sequences of the primers and of the probe were the following: primer forward: 5'-GGC ACA CGT GGC TTT TCG-3'(SEQ ID NO: 1); primer reverse: 5'-GGT GAA CCT CGT AAG TTT ATG CAA-3'(SEQ ID NO: 2); probe: VIC5'-TCA GGA CGT CGA GTG GAC ACG GTG-3'(SEQ ID NO: 3) TAMRA.

Fluorogenic PCRs were carried out in a reaction volume of 50 µl on a GeneAmp© 5700 Sequence Detection System (Applied Biosystem, Foster City, Calif.). Fluorogenic probe and primers were custom synthesized by Applied Biosystems. Each PCR reaction mixture consisted of: 25 µl of Taq- Man© Universal Master Mix Applied Biosystem; 0.67 μl probe [15 mM]; 0.45 μl primer forward [10 mM]; 0.45 μl primer reverse [10 mM]; 18.43 μl sterile water. 5 μl of DNA solution was used in each real-time PCR reaction. Thermal cycling was initiated with a first denaturation step of 50° C. for 2 min and then 95° C. for 10 min. The thermal profile for the PCR was 95° C. for 15 s and 60° C. for 1 min. Data obtained during 50 cycles of amplification were analyzed.

Amplifications were carried out in 96-well plates in a GeneAmp© 5700 Sequence Detection System (Applied Biosystem). Each plate consisted of patient samples in triplicates and multiple water blanks as negative control. For construction of the calibration curve on each plate we used a standard TaqMan Control Human Genomic DNA at 10 ng/μl (Applied Biosystem) with appropriate serial dilutions at 50 ng, 5 ng, 2.5 ng, 0.5 ng, 250 pg, 50 pg and 10 pg. Linear amplification down to the last dilution point representing 10 pg of target DNA was obtained in each experiment (Correlation coefficient 0.999-0.995; slope 3.25-3.35).

All the data were analysed using the Sequence Detection System software of Applied Biosystem to interpolate the standard amplification curve of DNA at known quantity with amplification CT of the unknown target sample thus obtaining the relative amount of DNA in the experimental sample.

For the follow-up study, all the consecutive plasma samples for each patient were simultaneously analysed in the same real-time PCR experiment to allow comparative quantification of samples along the observation time.

Pathological and Immunohistochemical Methods

Clinico-pathological data were available for all cases. There were 58 adenocarcinomas, 34 squamous cell carcinomas, 3 large cell carcinomas, 3 pleomorphic carcinomas, and 2 adenosquamous carcinomas. According to the WHO classification of lung adenocarcinoma (31), 19 (32.6%) showed acinar growth pattern, 19 papillary, 17 (29.3%) solid and 3 (5.2%) bronchioloalveolar. According to the revised lung cancer staging system (32), tumor stage was pT1 in 18%, pT2 in 55%, pT3 in 21% and pT4 in 6%; forty-seven percent of patients were pN0, 20% pN1 and 33% pN2 or N3. Stage I accounted for 34%, IIB 25%, IIIA 33%, and IIIB/IVB 8%. In three cases, the analysis was performed only on mediastinal nodes metastases.

In every case, the occurrence of either tumor necrosis or lymphoid infiltrate was evaluated semi-quantitatively on a scale from absent to 2+ (1+if $\leq$50%, and 2+ if >50% of the whole tumor). For immunohistochemical analysis, formalin-fixed and paraffin-embedded samples obtained at surgery were investigated for cell apoptosis-related (p53) and tumour growth (CD-117, Ki-67, and microvessel density) markers, according to previously refined methods (33). All cases were evaluated blindly without knowledge of the patients' identity, pathological diagnosis, clinical outcome or plasma DNA status. The percentage of p53-, EGFR-, CD117- and Ki-67-immunoreactive tumor cells was evaluated by scoring a minimum of 1,000 tumor cells in representative fields of immunostaining. Tumor neoangiogenesis was inferred by CD34 immunostaining of endothelial cells as previously described (34).

Statistical Methods

The distribution of DNA values revealed a departure from normality that was mitigated using a logarithmic transformation. The log of the concentration was used for testing purposes, however untransformed values were used for reporting results.

Odds ratios (OR) and corresponding 95% confidence intervals were calculated using conditional logistic regression in SAS (Cary, N.C., USA) to assess plasma DNA as a risk factor for NSCLC. A receiver-operating characteristic curve (ROC) was built to evaluate the diagnostic performance of plasma DNA concentrations. Each unique DNA value was used as cut-point to calculate sensitivity and specificity values defining the curve and the area under the curve (AUC). Standard errors were estimated separately as described in van der Schouw (35) in order to provide a 95% confidence interval for the area.

In cases, the possible association of DNA concentration with continuous clinical and pathologic parameters was explored calculating Pearson's or Spearman's correlation coefficients, depending on the distribution of the parameters (i.e. age and distribution of EGFR marker respectively). Comparison of median DNA plasma concentrations in patients with follow-up data was done using the Kruskal-Wallis test.

RESULTS

Quantitative Analysis of Circulating Plasma DNA in Cancer Patients and Controls

Figure 1:
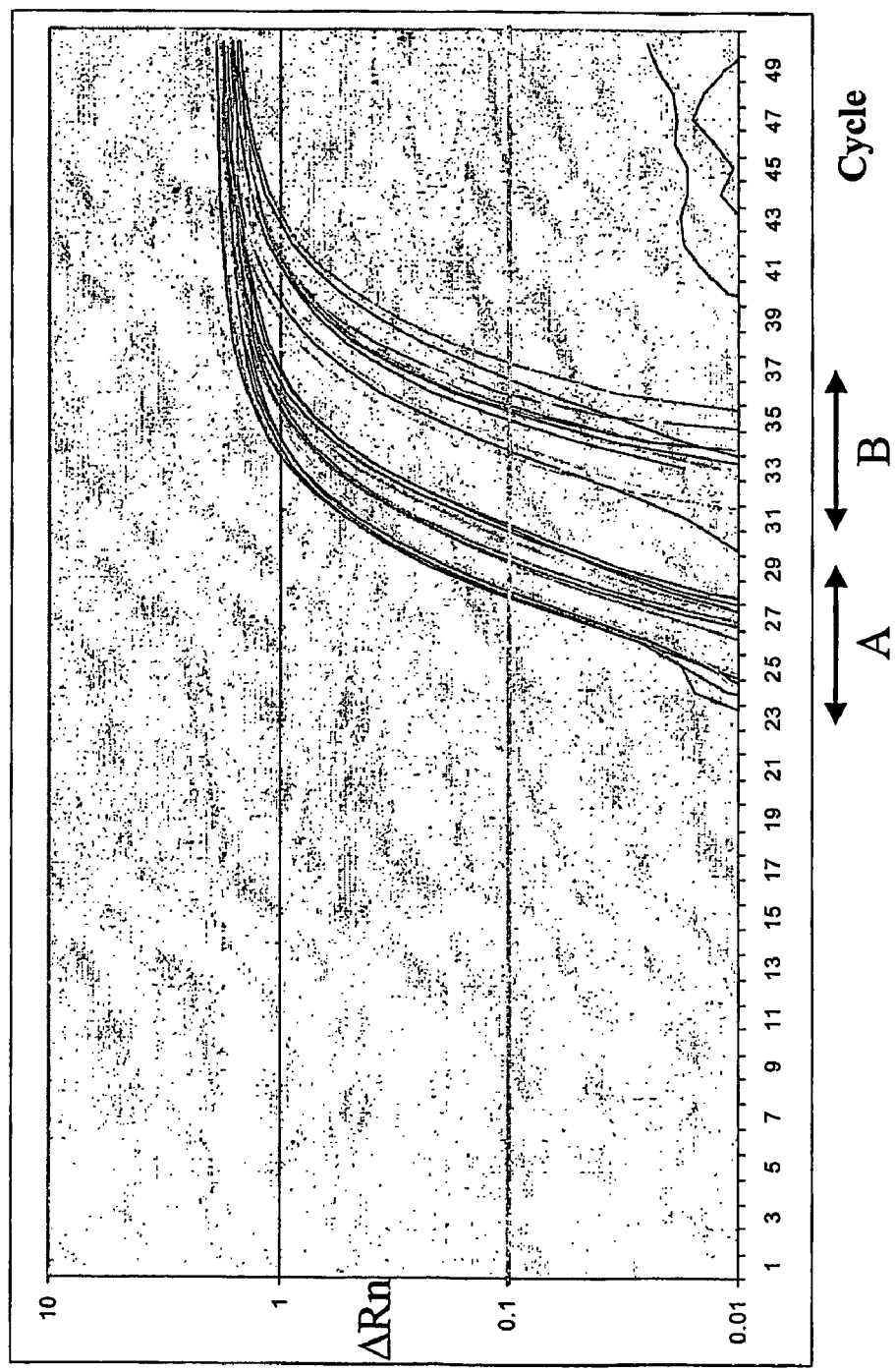
FIG. 1. Amplification plots of the real time quantitative PCR for hTERT in plasma DNA from NSCLC patients (A) and control samples (B). The relative amount of plasma DNA is much higher in patients samples (left plots) compared with controls (right plots).

FIG. 1 shows amplification plots of fluorescence intensity against the PCR cycle from plasma samples of cancer patients and matched controls. Each plot corresponds to the initial target DNA quantity present in the sample. The amplification curves shifted to the right, representing reduced target DNA quantity, clearly discriminate controls from cancer patients. The distribution of plasma DNA concentration in cases and matched controls describes two distinct populations of values despite some overlapping (FIG. 2). Median concentration in cases (24.3 ng/ml) was almost eight times the value detected in controls (3.1 ng/ml). Very high concentrations were observed only in cases, whereas at the other end of the distribution there were few cases with very low concentrations of DNA (i.e. 0.5 ng/ml). A greater variability of circulating DNA was observed in cases than in controls (see FIG. 2).

Plasma DNA Concentration as Risk Factor for NSCLC

An elevated concentration of circulating plasma DNA was associated with a higher risk of NSCLC. Tertile stratification showed that the risk increased exponentially when comparing subjects with plasma concentrations in the second and third tertile to those in the first tertile using conditional logistic regression (up to 85-fold, Table 1). When analyzed as continuous, a unit increase in plasma DNA (ng/ml) was associated with a 21% increase in NSCLC risk (OR=1.21, 95% cl=1.11, 1.31). Circulating DNA concentration was associated with age in cases (age coefficient when regressing the log of the plasma concentration=0.029, standard error=0.013, p=0.026). No association was observed between plasma DNA levels and smoking intensity or duration.

Diagnostic Performance of Quantitative Real-time PCR Assay

Figure 3:
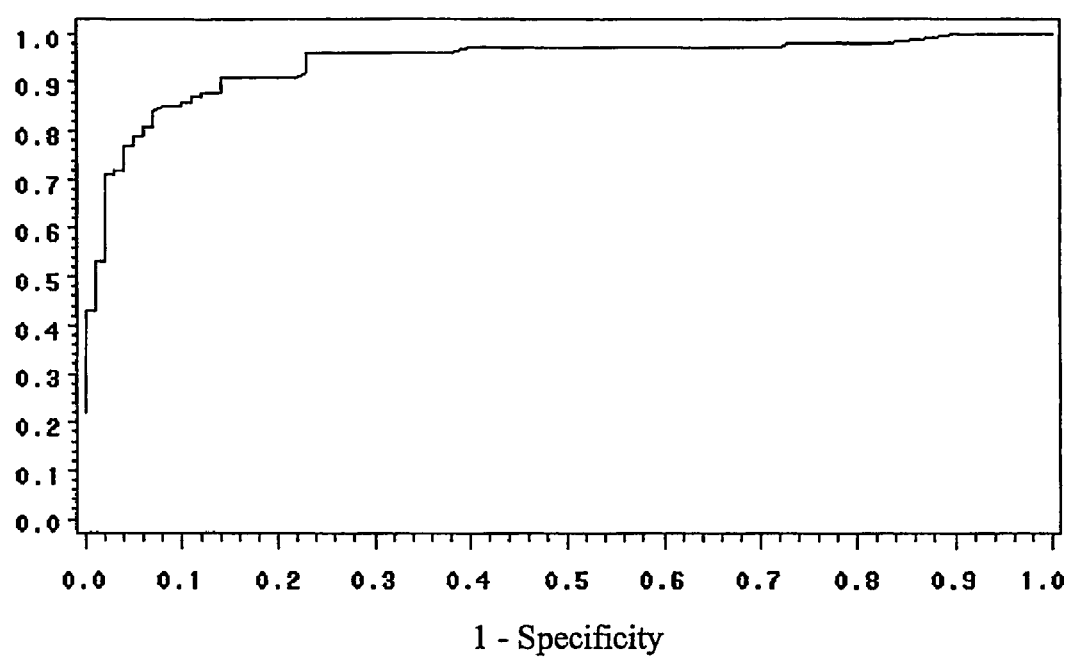

The area under the ROC curve shown in FIG. 3 was 0.94 (95% confidence interval 0.907-0.973) suggesting a strong discrimination power of the molecular assay. Shown in table 2 are few of the DNA concentration cut-points used to generate the curve with their sensitivity, specificity, positive predictive value and negative predictive value. The 95% confidence intervals around sensitivity estimates overlapped between the successive concentrations shown in table 2, except for the last two concentrations (20 and 25 ng/ml).

Correlation of Plasma DNA Levels with Clinico-pathological Features

Among the morphological and immunoistochemical markers analysed, a significant association with EGFR expression as well as with microvessel density were observed (table 3). The proliferation marker Ki67 increased with increasing plasma DNA concentration, although the correlation was not statistically significant (p=0.15). Age was the only clinical parameter that was significantly associated with DNA release in plasma. No association between plasma DNA levels and necrosis, lymphoid infiltration or growth patterns were observed.

Change in Plasma DNA Levels During Follow-up

In 35 out of the 100 cancer patients evaluated for the amounts of plasma DNA prior to surgery for Stage I-II tumors, a second plasma sample was obtained and analysed to monitor changes in DNA levels during clinical follow-up, 3 to 15 months after surgery (median elapsed time 8 months). The overall median DNA concentration in follow-up plasma samples was 8.4 ng/ml, showing a clear trend versus reduction when compared to median baseline levels of 24.5 ng/ml (p<0.0001). When comparing these patients according to their clinical status, median DNA concentration at follow-up was significantly lower in 30 disease-free subjects as compared to 5 cancer patients showing relapse (7.1 ng/ml versus 24.7 ng/ml; p=0.002).

TABLE 1

Plasma DNA concentration as risk factor for NSCLC

| | Controls N = 100 | Controls N = 100 | Odds Ratio Conditional * | 95% CI |
|---|---|---|---|---|
| | Distribution in tertiles of DNA in ng/ml † | | | |
| <=4 | 4 | 62 | 1 ‡ | |
| 4.1-20 | 27 | 36 | 5.5 | (1.9-16.3) |
| >20 | 69 | 2 | 85.5 | (16.5-445) |

* adjusted for age
† Obtained from the pooled distribution of plasma DNA values in cases and in controls.
‡ Reference group

TABLE 2

Screening performance of plasma DNA concentration

| Cut-point (ng/mL)* | Sensitivity | 95% CI† | Specificity | 95% CI† | PPV | NPV |
|---|---|---|---|---|---|---|
| 4 | 97 | 91.5-99.4 | 60 | 49.7-69.7 | 71 | 95 |
| 7 | 92 | 84.8-96.5 | 77 | 67.5-84.8 | 80 | 91 |
| 10 | 88 | 80.0-93.6 | 86 | 77.6-92.1 | 88 | 88 |
| 15 | 78 | 68.6-85.7 | 95 | 88.7-98.4 | 94 | 81 |
| 20 | 69 | 58.9-77.9 | 98 | 93.0-99.8 | 97 | 76 |
| 25 | 79 | 35.9-56.3 | 99 | 94.5-100 | 98 | 65 |

PPV = positive predictive value,
NPV = negative predictive value
*Contrasting concentrations lower than the cutpoint vs concentrations equal to or higher than the specified value
†Sensitivity and specificity estimates were treated as binomial parameteres to calculate 95% confidence intervals using Statxact (Cambridge, MA)

TABLE 3

Correlation of plasma DNA levels with clinico-pathological parameters
Log (DNA concentration)

| | Age | Smoking years | Log MVD | Ki67 | Egfr |
|---|---|---|---|---|---|
| Coefficient* | 0.22 | 0.04 | 0.25 | 0.15 | 0.2† |
| P Value | 0.026 | 0.71 | 0.016 | 0.15 | 0.044 |
| n‡ | 100 | 93 | 97 | 97 | 97 |

*Pearson's correlation coefficients
†Spearman's correlation coefficients
‡Sample size reduced to 93 controls of smokers (current or former) and 97 controls with primary cancer samples.

The invention claimed is:

1. A method for evaluating the risk of cancer in a smoker by determining the concentration of circulating total DNA in a plasma specimen from said smoker, which comprises:
 1) extracting the DNA from the plasma specimen obtained from a subject who smokes to create a target DNA sample;
 2) adding to the target DNA sample: a) a mixture of oligonucleotide primers suitable for PCR amplification of a fragment of the human telomerase reverse transcriptase (hTERT) gene, wherein said fragment of the hTERT gene is from nucleotide position 13059 to nucleotide position 13156 of the sequence of GenBank accession no. AF128893, and b) an oligonucleotide probe, having at least one quencher and one reporter fluorophore at the 3' and 5' ends, able to anneal to a sequence within the region delimited by the primers, in suitable conditions for carrying out a PCR reaction,
 3) adding a heat-stable DNA polymerase with 5'-3' exonuclease activity and amplifying the hTERT gene fragment;
 4) measuring the produced fluorescence;
 5) quantifying the hTERT DNA copy number in the target DNA sample interpolating a calibration curve created with known amounts of DNA, wherein the concentration of circulating total DNA in a plasma sample is determined by quantification of hTERT copy number
 6) correlating the hTERT copy number to the risk of cancer in the subject.

2. A method as claimed in claim 1, which further comprises comparing the concentration of circulating DNA to a reference concentration.

3. A method according to claim 2, wherein the reference concentration is from 9 to 25 ng/ml.

4. A method according to claim 1, wherein said fragment of the human telomerase reverse transcriptase (hTERT) gene is amplified using SEQ ID NO: 1 and 2 as the primers forward and reverse, respectively, and SEQ ID NO: 3 as the probe.

5. A method of evaluating the risk of developing cancer in a subject by determining the concentration of circulating total DNA in a plasma specimen from the subject, which comprises:
 1) extracting the DNA from the plasma specimen obtained from the subject to create a target DNA sample;
 2) adding to the target DNA sample: a) a mixture of oligonucleotide primers suitable for PCR amplification of a fragment of the human telomerase reverse transcriptase (hTERT) gene, wherein said fragment of the hTERT gene is from nucleotide position 13059 to nucleotide position 13156 of the sequence of GenBank accession no. AF128893, and b) an oligonucleotide probe, having at least one quencher and one reporter fluorophore at the 3' and 5' ends, able to anneal to a sequence within the region delimited by the primers, in suitable conditions for carrying out a PCR reaction,
 3) adding a heat-stable DNA polymerase with 5'-3' exonuclease activity and amplifying the hTERT gene fragment;
 4) measuring the produced fluorescence;
 5) quantifying the hTERT DNA copy number in the target DNA sample interpolating a calibration curve created with known amounts of DNA, wherein the concentration of circulating total DNA in a plasma sample is determined by quantification of hTERT copy number
 6) correlating the hTERT copy number to the risk of cancer in the subject.

6. A method as claimed in claim 1, wherein said cancer is lung, colon-rectum, head and neck, liver or pancreas cancer.

7. A method as claimed in claim 6, wherein said cancer is lung carcinoma.

8. The method as claimed in claim 5, wherein the subject is a cancer patient and said method is further used for the early diagnosis, prognosis or clinical monitoring of said cancer patient.

9. The method of claim 8, wherein the subject is a healthy individual.

10. The method of claim 8, wherein the subject is an individual with familial cancer susceptibility.

* * * * *

SEQUENCE LISTING

<160> NUMBER OF SEQ ID NOS: 3

<210> SEQ ID NO 1
<211> LENGTH: 18
<212> TYPE: DNA
<213> ORGANISM: Homo sapiens

<400> SEQUENCE: 1
ggcacacgtg gcttttcg                                                 18

<210> SEQ ID NO 2
<211> LENGTH: 24
<212> TYPE: DNA
<213> ORGANISM: Homo sapiens

<400> SEQUENCE: 2
ggtgaacctc gtaagtttat gcaa                                          24

<210> SEQ ID NO 3
<211> LENGTH: 24
<212> TYPE: DNA
<213> ORGANISM: Homo sapiens

<400> SEQUENCE: 3
tcaggacgtc gagtggacac ggtg                                          24